(12) United States Patent
O'Donnell et al.

(10) Patent No.: US 9,354,221 B2
(45) Date of Patent: May 31, 2016

(54) TURBOMACHINE LUBRICATING OIL ANALYZER SYSTEM, COMPUTER PROGRAM PRODUCT AND RELATED METHODS

(71) Applicant: General Electric Company, Schenectady, NY (US)

(72) Inventors: Keegan Saunders O'Donnell, Greenville, SC (US); Matthew Paul Fitzpatrick, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 581 days.

(21) Appl. No.: 13/872,488

(22) Filed: Apr. 29, 2013

(65) Prior Publication Data

US 2014/0324361 A1   Oct. 30, 2014

(51) Int. Cl.
*G01N 33/00* (2006.01)
*G01N 33/28* (2006.01)

(52) U.S. Cl.
CPC .................. *G01N 33/2888* (2013.01)

(58) Field of Classification Search
CPC ..... G01N 33/288; F01M 11/10; F01M 11/12; F01M 2011/14; F01D 25/20; G07C 5/006
See application file for complete search history.

(56) References Cited

U.S. PATENT DOCUMENTS

| | | |
|---|---|---|
| 4,677,847 A | 7/1987 | Sawatari et al. |
| 4,764,258 A | 8/1988 | Kauffman |
| 5,060,156 A | 10/1991 | Vajgart et al. |
| 5,382,942 A | 1/1995 | Raffa et al. |
| 5,604,441 A | 2/1997 | Freese et al. |
| 5,633,796 A | 5/1997 | Cullen et al. |
| 5,754,055 A | 5/1998 | McAdoo et al. |
| 5,914,890 A | 6/1999 | Sarangapani et al. |
| 5,968,371 A | 10/1999 | Verdegan et al. |
| 5,987,976 A | 11/1999 | Sarangapani |
| 6,128,561 A | 10/2000 | Janata |
| 6,297,733 B1 | 10/2001 | Park |
| 6,327,900 B1 | 12/2001 | McDonald et al. |
| 6,377,052 B1 | 4/2002 | McGinnis et al. |
| 6,449,538 B1 | 9/2002 | Kubo et al. |
| 6,457,564 B1 | 10/2002 | Damm et al. |
| 6,463,967 B1 | 10/2002 | Boyle |

(Continued)

OTHER PUBLICATIONS

U.S. Appl. No. 13/872,495, Office Action dated Sep. 18, 2015, (GEEN-0502), 20 pgs.

(Continued)

*Primary Examiner* — Elias Desta
(74) *Attorney, Agent, or Firm* — Ernest G. Cusick; Hoffman Warnick LLC (57) ABSTRACT

Various embodiments of the invention include a system having: at least one computing device at least one computing device configured to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the initial ideal remaining life, and the temperature-based remaining life; and determining an actual life remaining for the lubrication oil based upon the updated ideal life remaining and a life loss factor.

16 Claims, 6 Drawing Sheets

(56) References Cited

U.S. PATENT DOCUMENTS

| | | |
|---|---|---|
| 6,509,749 B1 | 1/2003 | Buelna et al. |
| 6,525,334 B1 | 2/2003 | Brackett |
| 6,741,938 B2 * | 5/2004 | Berndorfer ............ F01M 11/10 701/29.5 |
| 6,844,745 B1 | 1/2005 | Schachameyer et al. |
| 6,874,459 B2 | 4/2005 | Carey et al. |
| 7,370,514 B2 | 5/2008 | Halalay et al. |
| 7,581,434 B1 | 9/2009 | Discezo et al. |
| 7,928,741 B2 | 4/2011 | Hedges et al. |
| 8,082,115 B2 | 12/2011 | Bechhoefer et al. |
| 2003/0183188 A1 | 10/2003 | Carey et al. |
| 2003/0222656 A1 | 12/2003 | Phillips et al. |
| 2006/0161397 A1 | 7/2006 | Hayzen et al. |
| 2006/0169031 A1 | 8/2006 | Song et al. |
| 2008/0027661 A1 | 1/2008 | Aikawa |
| 2008/0087072 A1 | 4/2008 | Asher et al. |
| 2008/0163678 A1 | 7/2008 | Snider et al. |
| 2009/0063060 A1 | 3/2009 | Sun |
| 2009/0145211 A1 | 6/2009 | Schneider |
| 2009/0216471 A1 | 8/2009 | Akiyama et al. |
| 2010/0109686 A1 | 5/2010 | Zhe et al. |
| 2010/0299080 A1 | 11/2010 | Willmann et al. |
| 2013/0226392 A1 * | 8/2013 | Schneider .............. F01M 11/10 701/29.5 |
| 2013/0277147 A1 | 10/2013 | Conley et al. |

OTHER PUBLICATIONS

"Stanley Bracket webpage and detail drawing, copyright 2000, http://www.stanleyhardware.com/detail/110-shelf-brackets-n224-436".

U.S. Appl. No. 13/872,495, Notice of Allowance dated Dec. 3, 2015, (GEEN-502), 5 pages.

* cited by examiner

TURBOMACHINE LUBRICATING OIL ANALYZER SYSTEM, COMPUTER PROGRAM PRODUCT AND RELATED METHODS

CROSS-REFERENCE TO RELATED APPLICATION

This application relates to co-pending U.S. patent application Ser. No. 13/872,495, filed concurrently herewith on Apr. 29, 2013).

FIELD OF THE INVENTION

The subject matter disclosed herein relates to turbomachine systems. More particularly, the subject matter disclosed herein relates to lubrication oil in turbomachine systems, for example, gas turbomachines or steam turbomachines.

BACKGROUND OF THE INVENTION

Turbomachines, for example, gas turbines and/or steam turbines, use lubricating oil to reduce the frictional coefficient between machine components. While many turbomachines are delivered and installed by a manufacturing and/or selling entity, these turbomachines are frequently managed (over their lifetime) by the customer that purchases the turbomachine. In order to ensure that the lubricating oil in the turbomachine maintains a sufficient quality level to provide lubrication, the customer conventionally draws a sample of the oil and sends it to a laboratory for testing. However, some customers improperly draw the oil samples, which can compromise accuracy of the testing. Others do not draw samples frequently enough to properly monitor the condition of the oil.

In other industries, for example, the automotive industry, lubricating oil quality is estimated using empirical data that is tied to an expected lifetime of the oil based upon performance parameters of an automobile. In these cases, an automobile's monitoring system monitors the performance of the vehicle, e.g., speed, acceleration, braking, etc., and based upon the performance of the vehicle, estimates a time at which the lubricating oil will degrade in quality. These automotive systems do not, however, test the lubricating oil to determine its quality.

Due to the deficiencies in the above-noted techniques for monitoring lubricating oil quality, it is difficult to accurately assess the quality of lubricating oil in a turbomachine.

BRIEF DESCRIPTION OF THE INVENTION

Various embodiments of the invention include a system having: at least one computing device configured to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the initial ideal remaining life, and the temperature-based remaining life; and determining an actual life remaining for the lubrication oil based upon the updated ideal life remaining and a life loss factor.

A first aspect of the invention includes a system having: at least one computing device configured to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the initial ideal remaining life, and the temperature-based remaining life; and determining an actual life remaining for the lubrication oil based upon the updated ideal life remaining and a life loss factor.

A second aspect of the invention includes a computer program product including program code, which when executed by one computing device, causes the at least one computing device to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the initial ideal remaining life, and the temperature-based remaining life; and determining an actual life remaining for the lubrication oil based upon the updated ideal life remaining and a life loss factor.

A third aspect of the invention includes a system including: at least one computing device configured to analyze a lubrication oil from a turbomachine by performing actions including: predicting an initial ideal remaining life for the lubrication oil; determining a temperature-based remaining life of the lubrication oil based upon a measured temperature of the lubrication oil; determining a contamination factor of the lubrication oil based upon a measured contaminant level of the lubrication oil; determining a life loss factor of the lubrication oil based upon the initial ideal remaining life, the temperature-based remaining life, and the contamination factor; determining an amount of life lost from the lubrication oil based upon the life loss factor and a sampled frequency of the lubrication oil; calculating a refined ideal remaining life for the lubrication oil based upon the amount of life lost and the initial ideal remaining life; and predicting an actual remaining life of the lubrication oil based upon the refined ideal remaining life and the life loss factor.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the subject matter disclosed herein relates to turbomachine systems. More particularly, the subject matter disclosed herein relates to lubrication oil in turbomachine systems, for example, gas turbomachines or steam turbomachines.

As noted herein, it can be difficult to effectively monitor the quality of lubricating oil in turbomachine systems, which can lead to undesirable degradation of the oil, and ultimately, damage the turbomachine that relies upon that oil for lubrication.

In contrast to conventional approaches, various embodiments of the invention include systems, computer program products and associated methods to analyze a lubricating oil using test data extracted from that oil. In various particular embodiments a system includes at least one computing device configured to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the ideal remaining life, and the temperature-based remaining life; and determining an actual life remaining for the lubrication oil based upon the updated ideal life remaining and a life loss factor.

Various additional embodiments include a computer program product comprising program code, which when executed by one computing device, causes the at least one computing device to monitor a lubrication oil by performing actions including: determining an initial ideal remaining life for the lubrication oil; determining a temperature-based remaining life for the lubrication oil based upon a temperature measurement of the lubrication oil; calculating a contamination factor of the lubrication oil based upon a contamination sample of the lubrication oil; determining an updated ideal life remaining for the lubrication oil based upon the contamination factor, the ideal remaining life, and the temperature-based remaining life; and determining an actual life remaining for the lubrication oil based upon the updated ideal life remaining and a life loss factor.

Various additional embodiments of the invention include a system including: at least one computing device configured to analyze a lubrication oil from a turbomachine by performing actions including: predicting an initial ideal remaining life for the lubrication oil; determining a temperature-based remaining life of the lubrication oil based upon a measured temperature of the lubrication oil; determining a contamination factor of the lubrication oil based upon a measured contaminant level of the lubrication oil; determining a life loss factor of the lubrication oil based upon the initial ideal remaining life, the temperature-based remaining life, and the contamination factor; determining an amount of life lost from the lubrication oil based upon the life loss factor and a sampled frequency of the lubrication oil; calculating a refined ideal remaining life for the lubrication oil based upon the amount of life lost and the initial ideal remaining life; and predicting an actual remaining life of the lubrication oil based upon the refined ideal remaining life and the life loss factor.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Figure 1:
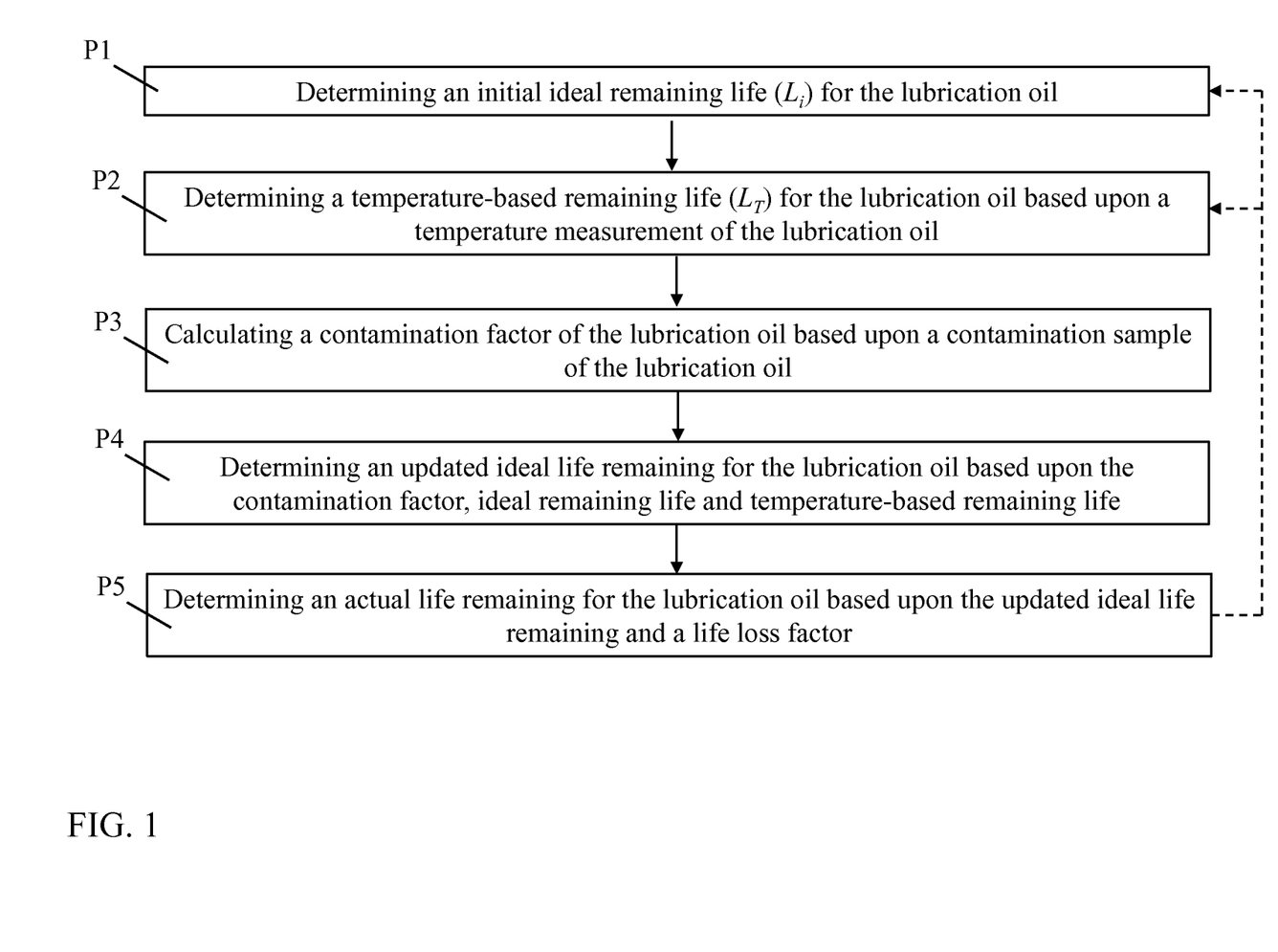
FIG. 1 shows a flow diagram illustrating a method performed according to various embodiments of the invention.

FIG. 1 shows a flow diagram illustrating a process of monitoring a lubrication oil (e.g., a lubrication oil in a turbomachine) according to various embodiments of the invention. These processes can be performed, e.g., by at least one computing device, as described herein. In other cases, these processes can be performed according to a computer-implemented method of monitoring a lubrication oil. In still other embodiments, these processes can be performed by executing computer program code on at least one computing device, causing the at least one computing device to monitor a lubrication oil. In general, the process can include the following sub-processes:

Process P1: determining an initial ideal remaining life ($L_i$) for the lubrication oil. In various embodiments, this includes obtaining information about the oil type, and calculating the Arrhenius Reaction Rate (ARR) for the oil type, assuming that the oil is clean (free of contaminants), and operates at its design temperature (optimal conditions). The initial ideal remaining life is the amount of life expected of the lubrication oil if it ran under these optimal conditions for its entire life.

The ARR is a known technique used to calculate the oxidation life drop (L) in a mineral oil. The ARR can be calculated according to the following equation in particular embodiments:

$$k = Ae^{-E_a/(RT)} \quad \text{(Equation 1)}$$

Where k=the rate constant of a chemical reaction; T=absolute temperature of the lubrication oil (in kelvin); A=the pre-exponential factor; $E_a$=the activation energy of the lubrication oil; and R=the Universal gas constant. Alternatively, the Universal gas constant (R) can be replaced with the Boltzmann constant ($k_B$). Simplified in the case of a mineral oil, the ARR can be represented in terms of an oxidation life (L) of the oil, the rate constant of the chemical reaction ($k_1$), and an ideal rate constant $k_2$=4750 as:

$$\text{Log}(L_i) = k_1 + (k_2/T) \quad \text{(Equation 2)}$$

Process P2: determining a temperature-based remaining life ($L_T$) for the lubrication oil based upon a temperature measurement of the lubrication oil. The temperature-based remaining life can represent an estimated life remaining as predicted based upon the measured temperature of the lubrication oil. This can include obtaining a measurement of the temperature of the lubrication oil. In the case that the lubrication oil is from a turbomachine, the temperature measurement may be obtained from a temperature sensor contacting the lubrication oil, either within the turbomachine, or external to the turbomachine. As with process P1, the temperature-based remaining life can be calculated according to the ARR.

Process P3 can include calculating a contamination factor of the lubrication oil based upon a (measured) contamination sample of the lubrication oil. In various embodiments, the calculating includes utilizing a transfer function to assign a qualitative weighted contamination factor to each of a plurality of measured oil properties noted herein. In various embodiments, a first oil property A is assigned a weighted contamination factor X, while a second oil property B is assigned a distinct weighted contamination factor of Y×X, where Y is a factor, e.g., 1, 2, 3, 0.1, 0.2, 0.3 a negative factor, percentage factor, etc. In various embodiments, the contamination sample can be obtained from a substantially similar sample of the lubrication oil as the temperature measurement. In various embodiments, the contamination sample is obtained and analyzed for at least one of the following oil properties: a ferrous particle count, water content, dielectric constant, and/or an international organization for standardization (ISO) particle level to calculate a contamination factor. In some particular cases, the ISO particle level includes an averaged ISO level particle count calculated from averaging a plurality of plurality of ISO level particle counts for the lubrication oil. In various cases, these can include an ISO 4 level particle count, an ISO 6 level particle count and ISO 14 level particle count.

Process P4 can include determining an updated ideal life remaining for the lubrication oil based upon the contamination factor, the ideal remaining life, and the temperature-based remaining life. In various embodiments, the updated ideal life remaining for the lubrication oil is calculated by subtracting an actual life (of the lubrication oil) lost from the initial ideal life remaining. In equation form: updated ideal life remaining=initial ideal life remaining−actual life lost. The actual life lost can be calculated by multiplying the life loss factor by a sample frequency of the lubrication oil. In equation form: actual life lost=life loss factor×sample frequency of the lubrication oil. The sample frequency can be obtained using a look-up table or other reference table, and can be calculated based upon a known relationship between the type of oil, the volume of oil in the reservoir, and the time between successive samplings of the oil. In various embodiments, these relationships are predetermined and saved, e.g., in memory or another data store within or accessible by at least one computing device (e.g., any computing device shown and/or described herein). Based upon a known frequency of the oil, and the measured volume of oil in the reservoir, the computing device can determine a time elapsed between samplings (e.g., successive samplings) of the oil. This time elapsed between samplings can be used to determine a remaining (and/or elapsed) life of the oil.

Process P5 can include determining an actual life remaining for the lubrication oil based upon the updated ideal life remaining and a life loss factor. In various embodiments, the actual life remaining is equivalent to the life loss factor times the sample frequency of the lubrication oil. In equation form: actual life lost=life loss factor×sample frequency of the lubrication oil. In various embodiments, the life loss factor is calculated by taking the ratio of the initial ideal remaining life to the temperature-based remaining life, and multiplying that ration by the contamination factor. In equation form: life loss factor=[initial ideal remaining life: temperature-based remaining life]×contamination factor.

In many embodiments, samples of the lubrication oil are obtained at various locations of the turbomachine. In these cases, it is understood that sample data may be averaged or otherwise normalized in order to determine a remaining life In some cases, for the first sample data (e.g., temperature data, contamination data, frequency data, etc.) obtained, the life loss factor can be multiplied by the time between obtaining samples and subtract the value from the life of the fluid under optimal conditions. As noted, this particular example applies to the case of the first sample obtained (or the first sample taken after oil has been changed out of the turbomachine and reservoir). After a first data sample is available, subsequent samples will form part of a running average that factors in some or all of the previously obtained samples.

In particular embodiments, the life loss factor can be calculated as a running average based upon a period of operation of the machine including the lubrication oil (e.g., a turbomachine). In some cases, the life loss factor is a running average taken over a recent (e.g., most recent) period such as the last 1-3 weeks of operation of the turbomachine.

In various embodiments, Processes P1-P5 can be iterated (repeated) periodically (e.g., according to schedule of x times per y period, and/or continuously) in order to monitor the actual life remaining for a lubrication oil. In some cases, processes P2-P5 can be repeated, for example, by obtaining new sample(s) of the lubrication oil and performing associated processes described herein. In these cases, process P1 may not need to be repeated because the initial ideal life remaining ($L_i$) may be substantially unchanged between some testing intervals.

Figure 2:
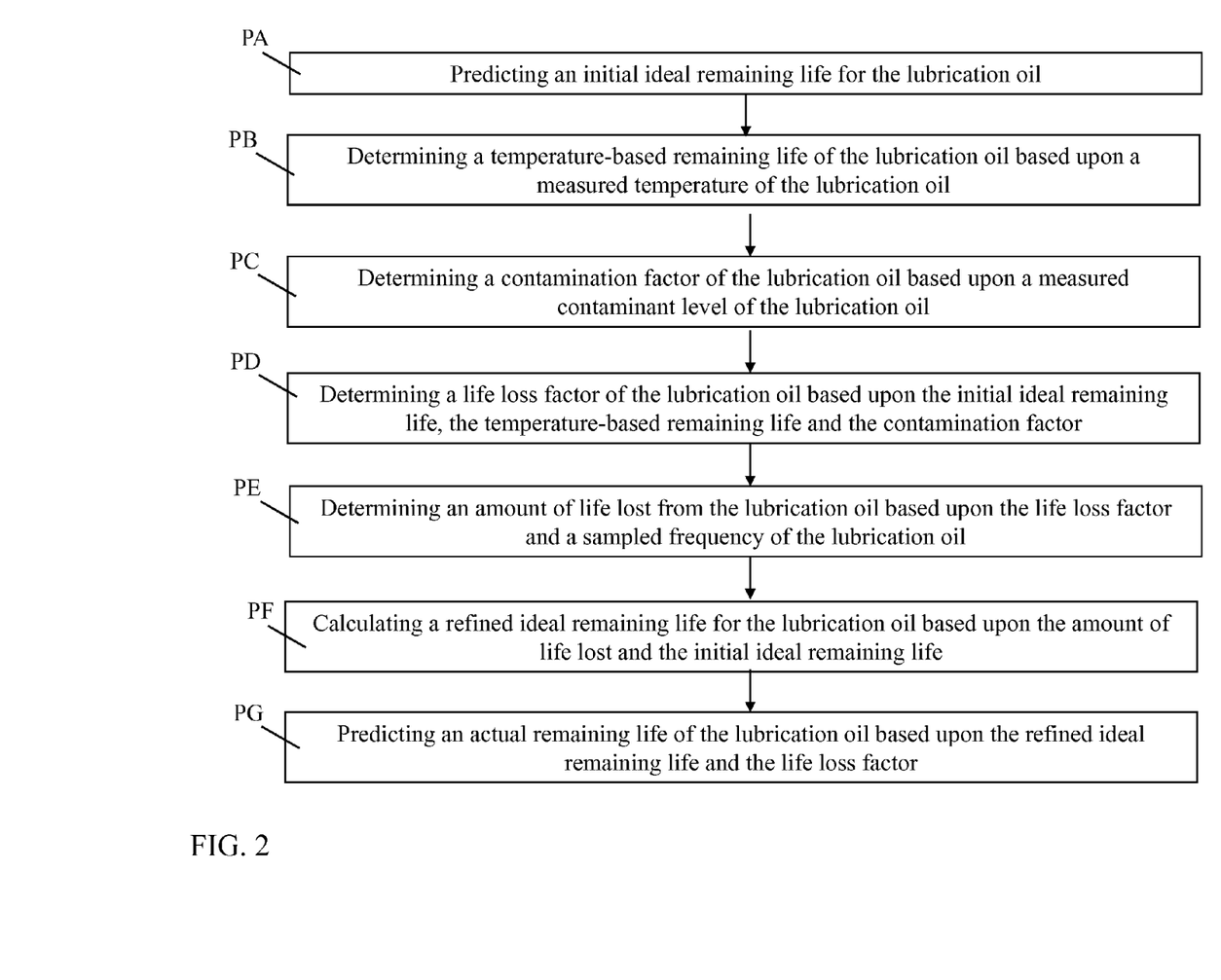
FIG. 2 shows a flow diagram illustrating a method performed to particular embodiments of the invention.

FIG. 2 shows a flow diagram illustrating a process of analyzing lubrication oil from a turbomachine according to various particular embodiments of the invention. These processes can be performed, e.g., by at least one computing device, as described herein. In other cases, these processes can be performed according to a computer-implemented method of monitoring a lubrication oil from a turbomachine. In still other embodiments, these processes can be performed by executing computer program code on at least one computing device, causing the at least one computing device to monitor a lubrication oil from a turbomachine. In general, the process can include the following sub-processes:

PA: predicting an initial ideal remaining life for the lubrication oil;

PB: determining a temperature-based remaining life of the lubrication oil based upon a measured temperature of the lubrication oil;

PC: determining a contamination factor of the lubrication oil based upon a measured contaminant level of the lubrication oil;

PD: determining a life loss factor of the lubrication oil based upon the initial ideal remaining life, the temperature-based remaining life, and the contamination factor;

PE: determining an amount of life lost from the lubrication oil based upon the life loss factor and a sampled frequency of the lubrication oil;

PF: calculating a refined ideal remaining life for the lubrication oil based upon the amount of life lost and the initial ideal remaining life; and PG: predicting an actual remaining life of the lubrication oil based upon the refined ideal remaining life and the life loss factor.

It is understood that in the flow diagrams shown and described herein, other processes may be performed while not being shown, and the order of processes can be rearranged according to various embodiments. Additionally, intermediate processes may be performed between one or more described processes. The flow of processes shown and described herein is not to be construed as limiting of the various embodiments.

Figure 3:
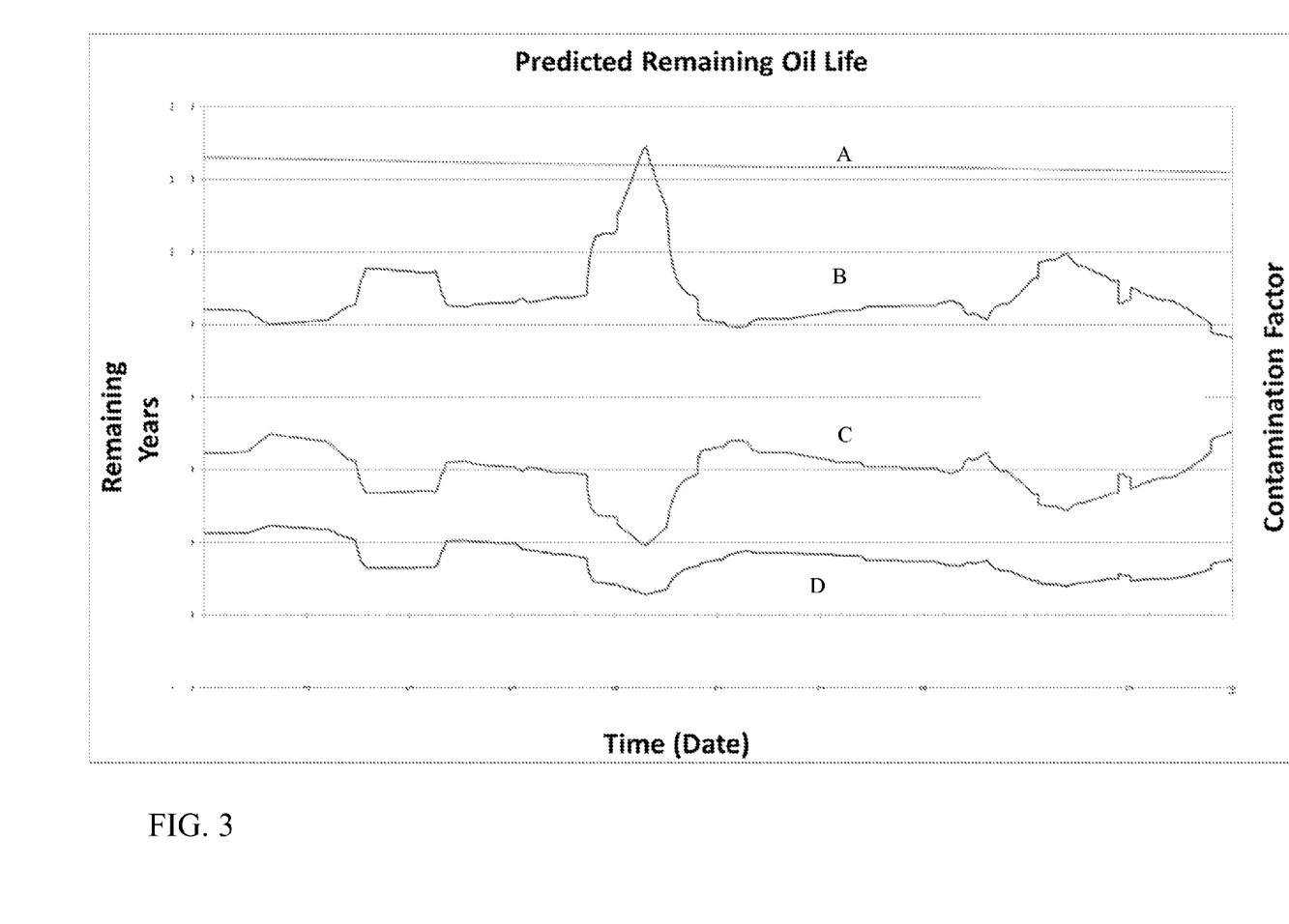
FIG. 3 shows a graphical depiction of oil lifetime predictions according to ideal estimates, as well as according to various embodiments of the invention.

FIG. 3 shows an example graphical depiction of predicted remaining oil life curves according to: A) A theoretical calculation of remaining oil life based upon ideal conditions; B) A contamination factor curve; C) An calculation of remaining oil life based upon an actual lifetime lost; and D) A calculation of remaining oil life based upon a factored remaining useful life calculation. Time in years is shown on the left Y-axis, contamination factor is shown on the right Y-axis and time is shown on the x axis.

Figure 4:
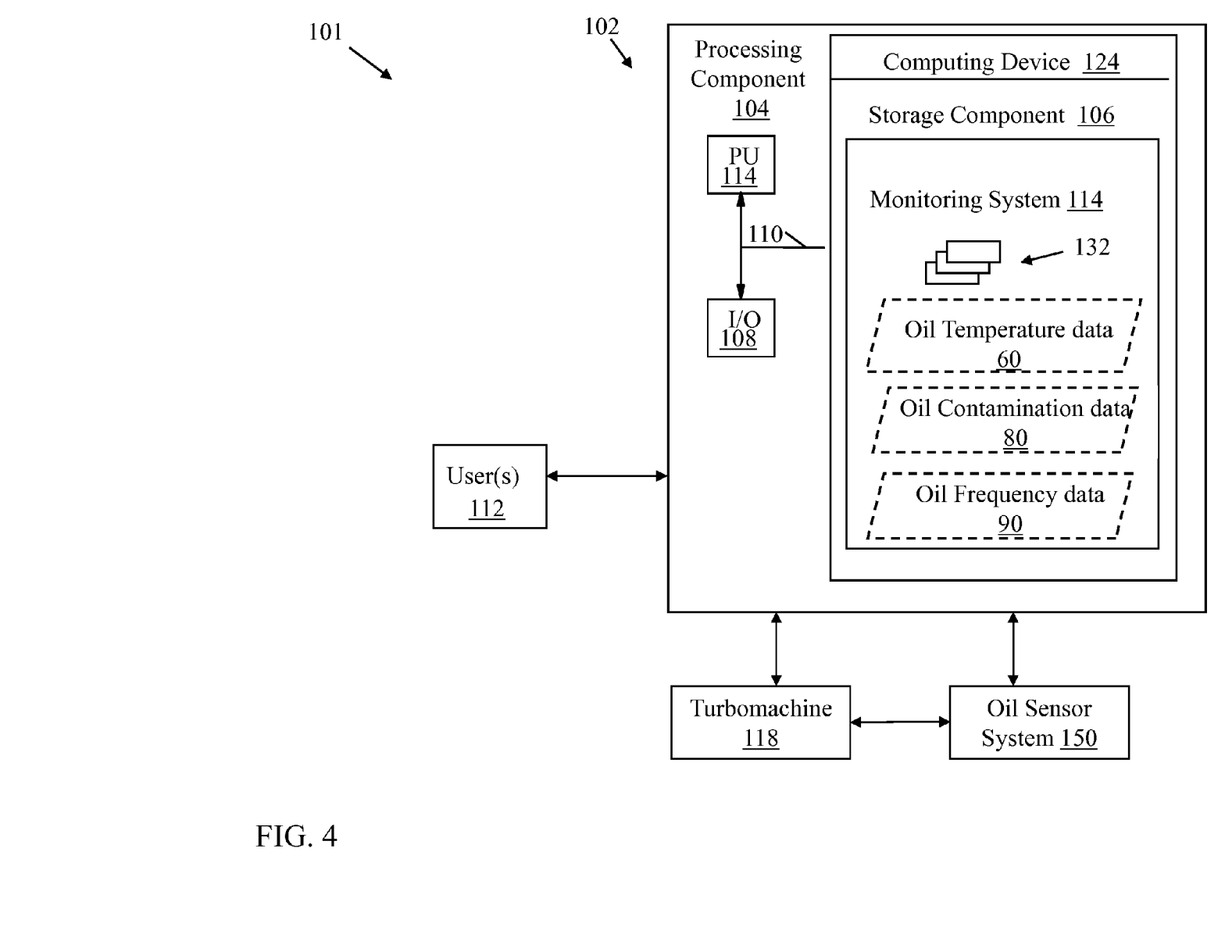
FIG. 4 shows an environment including a system according to various embodiments of the invention.

FIG. 4 shows an illustrative environment 101 including a monitoring system 114, for performing the functions described herein according to various embodiments of the invention. To this extent, the environment 101 includes a computer system 102 that can perform one or more processes described herein in order to monitor a lubrication oil, e.g., from a turbomachine. In particular, the computer system 102 is shown as including the monitoring system 114, which makes computer system 102 operable to monitor a lubrication oil by performing any/all of the processes described herein and implementing any/all of the embodiments described herein.

The computer system 102 is shown including a computing device 124, which can include a processing component 104 (e.g., one or more processors), a storage component 106 (e.g., a storage hierarchy), an input/output (I/O) component 108 (e.g., one or more I/O interfaces and/or devices), and a communications pathway 110. In general, the processing component 104 executes program code, such as the monitoring system 114, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O devices, which enable a user (e.g., a human and/or computerized user) 112 to interact with the computer system 102 and/or one or more communications devices to enable the system user 112 to communicate with the computer system 102 using any type of communications link. To this extent, the monitoring system 114 can manage a set of interfaces (e.g., graphical user interface(s), application program interface, etc.) that enable human and/or system users 112 to interact with the monitoring system 114. Further, the monitoring system 114 can manage (e.g., store, retrieve, create, manipulate, organize, present, etc.) data, such as oil temperature data 60 (e.g., data about the temperature of the oil, obtained by sensor system 150), oil contamination data 80 (e.g., data about the contamination level of the oil, obtained by sensor system 150) and/or oil frequency data 90 (e.g., data about the frequency measurement of the oil, as obtained by sensor system 150) using any solution. The monitoring system 114 can additionally communicate with a turbomachine 118 and/or an oil sensor system 150 via wireless and/or hardwired means.

In any event, the computer system 102 can comprise one or more general purpose computing articles of manufacture (e.g., computing devices) capable of executing program code, such as the monitoring system 114, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the monitoring system 114 can be embodied as any combination of system software and/or application software. It is further understood that the monitoring system 114 can be implemented in a cloud-based computing environment, where one or more processes are performed at distinct computing devices (e.g., a plurality of computing devices 24), where one or more of those distinct computing devices may contain only some of the components shown and described with respect to the computing device 124 of FIG. 4.

Further, the monitoring system 114 can be implemented using a set of modules 132. In this case, a module 132 can enable the computer system 102 to perform a set of tasks used by the monitoring system 114, and can be separately developed and/or implemented apart from other portions of the monitoring system 114. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of monitoring system 114 fixed thereon (e.g., one or more modules 132). However, it is understood that the computer system 102 and monitoring system 114 are only representative of various possible equivalent computer systems that may perform a process described herein. To this extent, in other embodiments, the functionality provided by the computer system 102 and monitoring system 114 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices 124, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide data, such as oil temperature data 60, oil contamination data 80 and/or oil frequency data 90 using any solution. The computer system 102 can generate oil temperature data 60, oil contamination data 80 and/or oil frequency data 90, from one or more data stores, receive oil temperature data 60, oil contamination data 80 and/or oil frequency data 90, from another system such as the turbomachine 118, oil sensor system 150 and/or the user 112, send probe transmission data 60 and/or probe reception data 80 to another system, etc.

While shown and described herein as a method and system for monitoring a lubrication oil, it is understood that aspects of the invention further provide various alternative embodiments. For example, in one embodiment, the invention provides a computer program fixed in at least one computer-readable medium, which when executed, enables a computer system to monitor a lubrication oil. To this extent, the computer-readable medium includes program code, such as the monitoring system 114 (FIG. 4), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the monitoring system 114 (FIG. 4), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of monitoring a lubrication oil. In this case, a computer system, such as the computer system 102 (FIG. 4), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the various embodiments of the invention, including, e.g., the monitoring system 114, is to monitor a lubrication oil, e.g., a lubrication oil from a turbomachine (e.g., turbomachine 118). It is understood that the monitoring system 114 could be implemented monitor a lubrication oil in a plurality of distinct applications, e.g., to monitor lubrication oil in an automobile system, to monitor lubrication oil in a piece of heavy machinery, etc.

Various additional embodiments can include a lubricating oil monitoring apparatus, which can include one or more components of the monitoring system 114 (and associated functionality), along with the oil sensor system 150. The lubricating oil monitoring apparatus can be configured to non-invasively monitor one or more condition(s) of the lubricating oil. In some cases, the lubricating oil monitoring apparatus (and in particular, the oil sensor system 150) can monitor one or more parameters of the lubricating oil, including but not limited to: an International Organization of Standards (ISO) particle count, a ferrous material particle count, a water content and/or a chemical breakdown.

In various embodiments, the lubricating oil monitoring apparatus can continuously monitor these parameters, and compare these parameters with acceptable thresholds (e.g., levels or ranges) to determine whether the lubricating oil is at a desired level. The lubricating oil monitoring apparatus can include an interface, e.g., a human-machine interface (HMI) for providing one or more alerts when the determined parameter(s) of the lubricating oil deviate, approach, and/or trend toward an unacceptable threshold/range.

In some cases, the lubricating oil monitoring apparatus can be mounted or otherwise coupled with the turbomachine. In other cases, the lubricating oil monitoring apparatus is located proximate the turbomachine to provide real-time monitoring of the condition of the lubricating oil.

In various embodiments, the lubricating oil monitoring apparatus can be fluidly connected with the existing lubricating oil reservoir in the turbomachine. In some particular embodiments, the lubricating oil monitoring apparatus is fluidly connected with the return line drain section of the oil reservoir. In some cases, the lubricating oil monitoring apparatus includes an oil supply line for extracting oil from the reservoir, and a drain line for draining tested oil back to the reservoir. The apparatus can also include a mount for mounting onto the reservoir or a proximate portion of the turbomachine.

Figure 5:
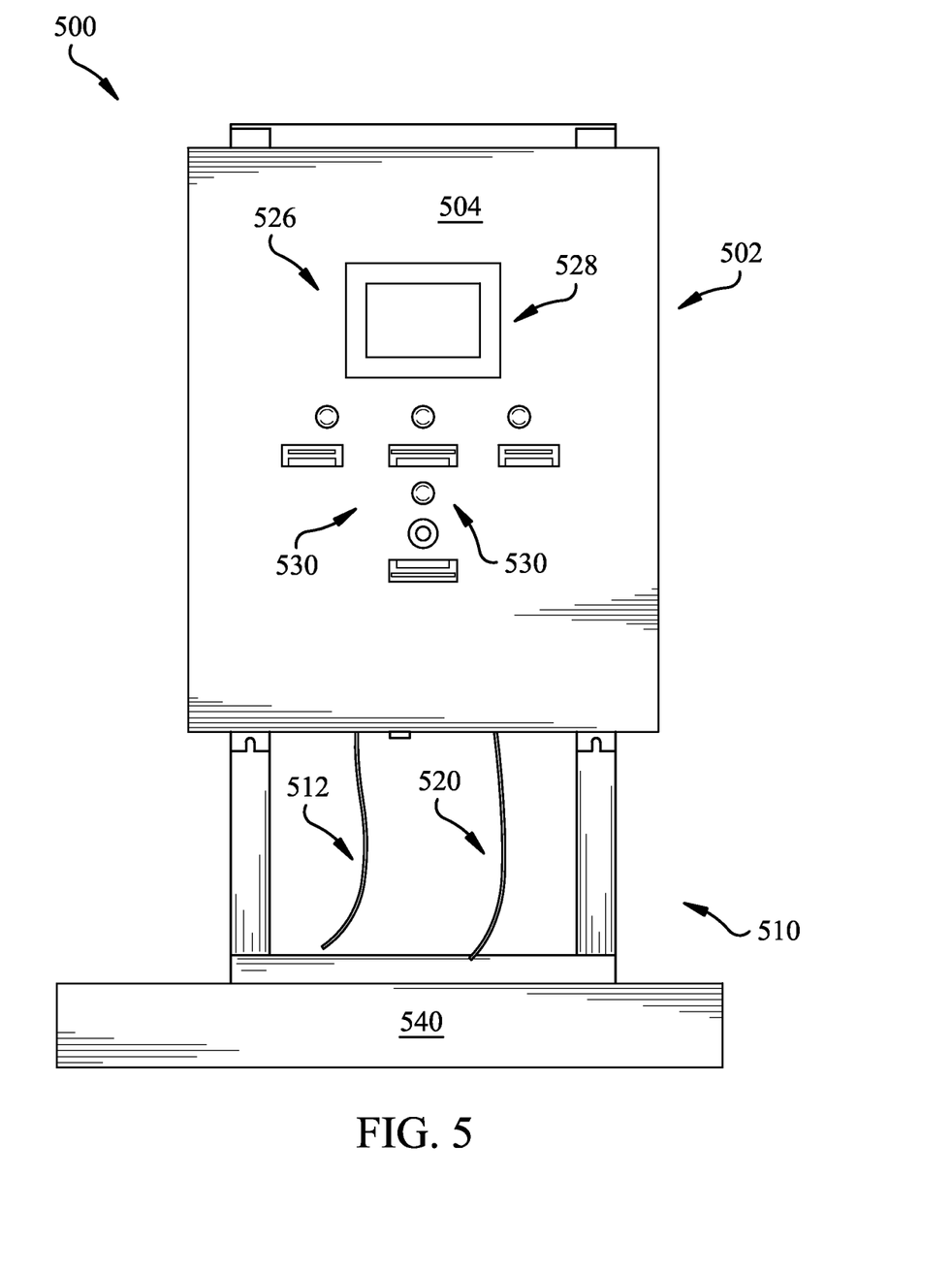
FIG. 5 shows a front schematic view of an apparatus according to various embodiments of the invention.
Figure 6:
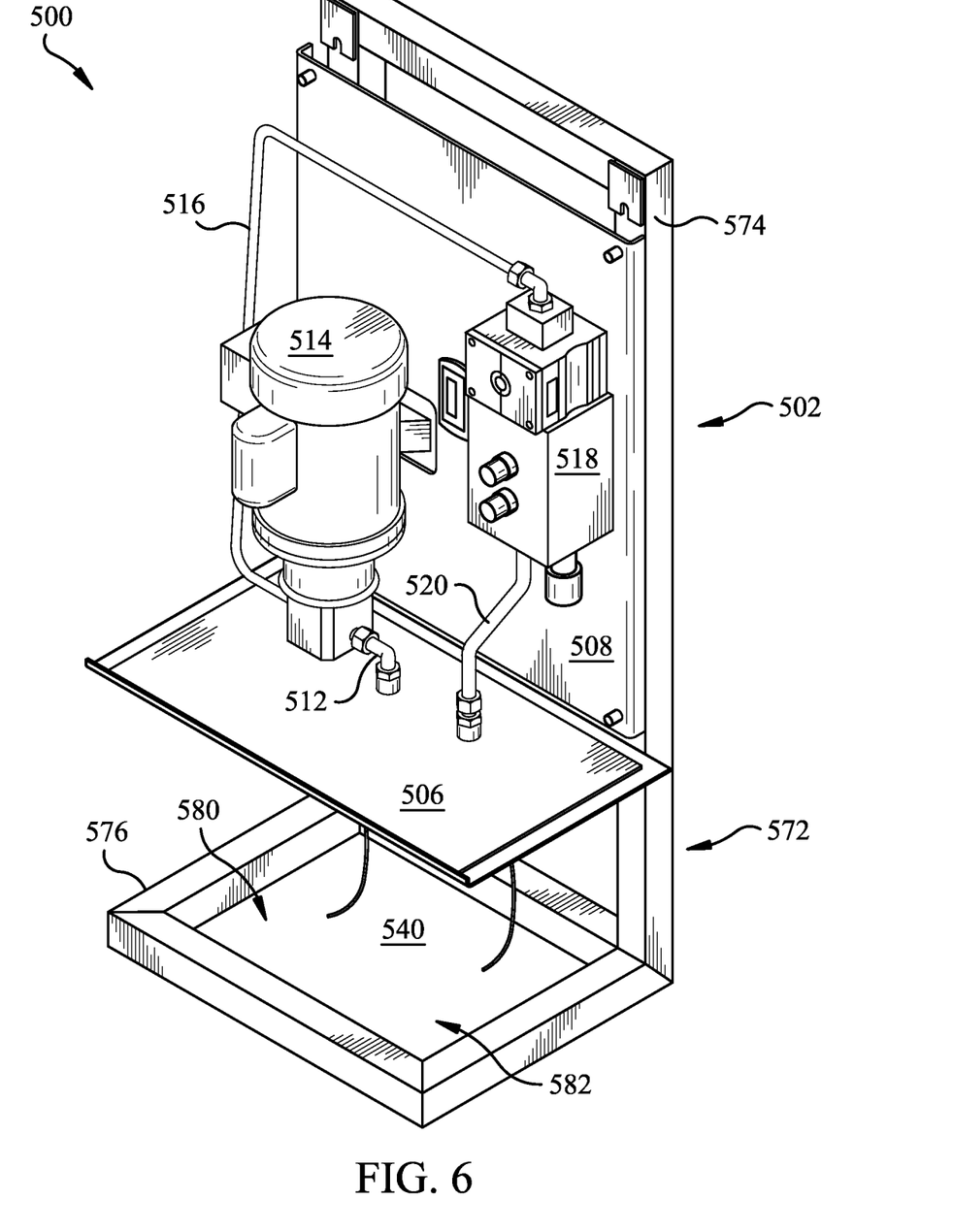
FIG. 6 shows a partial perspective view of the apparatus of FIG. 5 according to embodiments of the invention.

FIGS. 5 and 6 show a schematic front view and partial perspective view, respectively, of a lubricating oil monitoring apparatus (apparatus) 500 according to various embodiments of the invention. FIG. 5 shows the apparatus 500 including a housing section 502 having a casing 504 over a base plate 506 and back support 508 (FIG. 6). FIG. 5 also illustrates a mount 510 coupled with the housing section 502. FIG. 6 shows the apparatus 500 in perspective view without the casing 504, and illustrates the oil intake conduit 512, oil pump 514, internal conduit 516, oil analyzer 518, and drain conduit 520. Various components described with respect to the apparatus 500 can be formed of conventional materials known in the art, e.g., metals such as steel, copper, aluminum, alloys, composites, etc.

With reference to both FIGS. 5 and 6, in some particular embodiments, the lubricating oil monitoring apparatus (apparatus) 500 can include:

A housing section 502 including a base plate 506 and back support 508, which may be formed of a sheet metal or other suitable composite. The housing section 502 can also include a casing 504 coupled to the base plate 506 and the back support 508, as shown in FIG. 5. In various embodiments, the casing can include an interface 526, e.g., a human-machine interface (HMI), which can include a display 528 (e.g., a touch-screen, digital or other display). In some cases, the interface 526 can include one or more alert indicator(s) 530, which can include one or more lights (e.g., LEDs), audio indicators and/or tactile indicators for indicating that a condition of the tested oil is approaching, has approached or could approach an undesirable level (e.g., range).

The housing section 502 can also include an oil intake conduit 512 connected with the base plate 506 and extending through the base plate 506. The oil intake conduit 512 can be fluidly connected with the turbomachine oil reservoir (reservoir) 540, and is configured to extract oil from the reservoir 540. Also shown (in FIG. 6), the housing section 502 can include an oil pump 514 substantially contained within the casing 504 and fluidly connected with the oil intake conduit 512. The pump 514 can provide pumping pressure to draw the oil from the reservoir 540 through the oil intake conduit 512 (and above the base plate 506). The housing section 502 can further include an internal conduit 516 fluidly connected with the oil pump 514 (at an outlet of the pump 514) and the intake conduit 512. The internal conduit 516 is configured for receiving intake oil from the pump 514. The housing section 502 can also include an oil analyzer 518 fluidly connected with the internal conduit 516, where the oil analyzer 518 measures a characteristic of the intake oil (e.g., a particle count/ISO level, a ferrous particle count, a water content, a temperature and/or a dielectric constant). Also shown, the housing section 502 can include a drain conduit 520 fluidly connected with the oil analyzer 518, extending through the base plate 506, and fluidly connected with the reservoir 540. The drain conduit 520 allows for draining of tested oil back to the reservoir 540.

The apparatus 500 can also include a mount 570 coupled to the housing section 502. The mount 510 can be designed to couple to the oil reservoir 540 of a turbomachine.

In various embodiments, the base plate 506 is configured to face vertically downward, e.g., run perpendicular to the vertical axis (y). This can allow the drain conduit 560 to utilize gravitational forces to drain the tested lubricating oil back to the reservoir 540. In these cases, the base plate 506 overlies the reservoir 540.

In some particular embodiments, the mount 510 includes an L-shaped member 572 including a vertically extending spine 574 coupled with the housing section 502 and a horizontally extending base 576. The horizontally extending base 576 can be mountable on the oil reservoir 540 of the turbomachine.

It is understood that the apparatus 500 can be powered by a power unit, e.g., a battery power unit, and/or a direct alternating-current (AC) connection with one or more power sources of the turbomachine.

During operation the apparatus 500 is configured to extract reservoir oil from the oil reservoir 540 via the intake conduit 512 (with the pump 514 providing the pressure to draw the reservoir oil vertically upward), pump that extracted oil through the internal conduit 516, and provide the oil to the analyzer 518 for testing prior to releasing the oil back to the reservoir 540 via the drain conduit 520. In various embodiments, the drain conduit 520 empties to a distinct section 580 of the reservoir 540 than the section 582 coupled with the intake conduit 512. In some cases, the reservoir 540 has a substantially continuous flow path going from the extraction location 582 toward the drain location 580, meaning that new oil is continuously entering the reservoir 540 from the turbomachine, passing through the reservoir 540 (and being tested by the apparatus 500), and re-entering the turbomachine.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
    at least one computing device configured to monitor a lubrication oil by performing actions including:
        determining, by a processor, an initial ideal remaining life for the lubrication oil;
        determining a temperature-based remaining life for the lubrication oil based upon a temperature measurement of the lubrication oil;
        calculating a contamination factor of the lubrication oil based upon a contamination sample of the lubrication oil,
        wherein the contamination factor is calculated based upon either: a measurement of at least one of the following properties of the lubrication oil: a ferrous particle count, a water content, a dielectric constant or an international organization for standardization (ISO) level particle count; or an averaged international organization for standardization (ISO) level particle count calculated from averaging a plurality of ISO level particle counts for the lubrication oil;
        determining an updated ideal life remaining for the lubrication oil based upon the contamination factor, the initial ideal remaining life, and the temperature-based remaining life; and
        determining an actual life remaining for the lubrication oil based upon the updated ideal life remaining and a life loss factor.

2. The system of claim 1, wherein the at least one computing device is further configured to determine the life loss factor according to the following:

life loss factor=[initial ideal remaining life: temperature-based remaining life]×contamination factor.

3. The system of claim 2, wherein the at least one computing device is further configured to determine an elapsed time between samplings of the lubrication oil based upon a sample frequency of the lubrication oil.

4. The system of claim 3, wherein the determining of the actual life remaining includes determining an actual life lost according to the following:

actual life lost=life loss factor×sample frequency of the lubrication oil.

5. The system of claim 4, wherein the determining of the updated ideal life remaining for the lubrication oil includes calculating the updated ideal life remaining according to:

updated ideal life remaining=initial ideal life remaining−actual life lost.

6. The system of claim 1, wherein the determining of the actual life remaining for the lubrication oil includes calculating the actual life remaining according to:

actual life remaining=updated ideal life remaining/life loss factor.

7. The system of claim 1, wherein the temperature-based remaining life for the lubrication oil is calculated based upon an Arrhenius Reaction Rate of the lubrication oil.

8. A computer program product comprising program code, which when executed by at least one computing device, causes the at least one computing device to monitor a lubrication oil by performing actions including:
  determining, by a processor, an initial ideal remaining life for the lubrication oil;
  determining a temperature-based remaining life for the lubrication oil based upon a temperature measurement of the lubrication oil;
  calculating a contamination factor of the lubrication oil based upon a contamination sample of the lubrication oil,
  wherein the contamination factor is calculated based upon either: a measurement of at least one of the following properties of the lubrication oil: a ferrous particle count, a water content, a dielectric constant or an international organization for standardization (ISO) level particle count; or an averaged international organization for standardization (ISO) level particle count calculated from averaging a plurality of ISO level particle counts for the lubrication oil;
  determining an updated ideal life remaining for the lubrication oil based upon the contamination factor, the initial ideal remaining life, and the temperature-based remaining life; and
  determining an actual life remaining for the lubrication oil based upon the updated ideal life remaining and a life loss factor.

9. The computer program product of claim 8, wherein the program code causes the at least one computing device to determine the life loss factor according to the following:

life loss factor=[initial ideal remaining life: temperature-based remaining life]×contamination factor.

10. The computer program product of claim 9, wherein the program code causes the at least one computing device to further obtain a sample frequency of the lubrication oil.

11. The computer program product of claim 10, wherein the determining of the actual life remaining includes determining an actual life lost according to the following:

actual life lost=life loss factor×sample frequency of the lubrication oil.

12. The computer program product of claim 11, wherein the determining of the updated ideal life remaining for the lubrication oil includes calculating the updated ideal life remaining according to:

updated ideal life remaining=initial ideal life remaining−actual life lost.

13. The computer program product of claim 8, wherein the determining of the actual life remaining for the lubrication oil includes calculating the actual life remaining according to:

actual life remaining=updated ideal life remaining/life loss factor.

14. A system comprising:
  at least one computing device configured to analyze a lubrication oil from a turbomachine by performing actions including:
    predicting, by a processor, an initial ideal remaining life for the lubrication oil;
    determining a temperature-based remaining life of the lubrication oil based upon a measured temperature of the lubrication oil;
    determining a contamination factor of the lubrication oil based upon a measured contaminant level of the lubrication oil,
    wherein the contamination factor is determined based upon either: a measurement of at least one of the following properties of the lubrication oil: a ferrous particle count, a water content, a dielectric constant or an international organization for standardization (ISO) level particle count; or an averaged international organization for standardization (ISO) level particle count calculated from averaging a plurality of ISO level particle counts for the lubrication oil;
    determining a life loss factor of the lubrication oil based upon the initial ideal remaining life, the temperature-based remaining life, and the contamination factor;
    determining an amount of life lost from the lubrication oil based upon the life loss factor and a sampled frequency of the lubrication oil;
    calculating a refined ideal remaining life for the lubrication oil based upon the amount of life lost and the initial ideal remaining life; and
    predicting an actual remaining life of the lubrication oil based upon the refined ideal remaining life and the life loss factor.

15. The system of claim 14, wherein the measured temperature of the lubrication oil is measured at a common location on the turbomachine as the measured contaminant level.

16. The system of claim 15, wherein the measured temperature of the lubrication oil is measured at a substantially same time as the measured contaminant level.

* * * * *